United States Patent [19]

Coughlin et al.

[11] 4,048,018

[45] * Sept. 13, 1977

[54] METHOD OF CARRYING OUT ENZYME CATALYZED REACTIONS

[76] Inventors: Robert W. Coughlin, 902 Seventh Ave., Bethlehem, Pa. 18018; Marvin Charles, 622 N. 29 St., Allentown, Pa. 18104

[ * ] Notice: The portion of the term of this patent subsequent to Apr. 5, 1994, has been disclaimed.

[21] Appl. No.: 665,300

[22] Filed: Mar. 9, 1976

Related U.S. Application Data

[60] Continuation-in-part of Ser. No. 495,073, Aug. 5, 1974, abandoned, which is a division of Ser. No. 228,748, Feb. 23, 1972, Pat. No. 3,928,143.

[51] Int. Cl.$^2$ .................................................. C12B 1/00
[52] U.S. Cl. ....................................... 195/115; 195/63; 195/68; 195/127; 195/139
[58] Field of Search ................... 195/115, 116, 63, 68, 195/31 F, 31 R, 139, 49, 127

[56] References Cited

U.S. PATENT DOCUMENTS

| | | | |
|---|---|---|---|
| 3,519,538 | 7/1970 | Messing et al. | 195/68 |
| 3,669,841 | 6/1972 | Miller | 195/63 |
| 3,767,535 | 10/1973 | Havewala et al. | 195/63 |
| 3,783,101 | 1/1974 | Tomb et al. | 195/63 |
| 3,791,927 | 2/1974 | Forgione et al. | 195/63 |

OTHER PUBLICATIONS

Barker et al., "Enzyme Reactors for Industry," Process Biochemistry, vol. 6, No. 10, (Oct. 1971), pp. 11–13.
Emery et al., "Some Applications of Solid-Phase Enzymes in Biological Engineering," Birmingham Univ. Chem. Engineer, vol. 22, 1971, pp. 37–45 No. 2 (Summer).

*Primary Examiner*—Raymond N. Jones
*Assistant Examiner*—Thomas G. Wiseman

[57] ABSTRACT

A liquid stream containing the reactants is passed through a bed of enzyme catalyst, made up of enzymes bonded to small, dense particles of carrier or support materials, in a manner which causes the bed to expand or fluidize and a chemical reaction is thereby carried out in a process that is simultaneously free from limitations due to plugging and excessive pressure drop and which also has the advantage of the high mass transfer rates that can be realized between the liquid and small particles.

13 Claims, No Drawings

METHOD OF CARRYING OUT ENZYME CATALYZED REACTIONS

This application is a continuation-in-part of application Ser. No. 495,073 filed Aug. 5, 1974, now abandoned, which application was in turn a division of application Ser. No. 228,748 filed Feb. 23, 1972; the last-cited application is now U.S. Pat. No. 3,928,143.

BACKGROUND OF THE INVENTION

1. Field of Invention

This invention relates to a method for carrying out chemical reactions using as catalysts enzymes that are insolubilized or immobilized by bonding them to solid supporting materials, and in which a solution of the chemical reactants passes upward through a bed of such solid supporting material to which the enzymes of choice have been bound, such supporting material being in the form of particles of the proper size and density and the reactant solution flowing through the bed at such a rate that the bed of particles becomes expanded or fluidized and the advantages of fluidized bed operation are conferred upon the system and process thereby realized.

2. Description of Prior Art

Within the last decade the art of attaching enzymes to insoluble supporting materials has been developed and such solid-bound enzyme catalysts can now be applied to practical, commercial processes such as producing glucose from starch, hydrolyzing proteins and sugars, clarifying fruit juices and beer, carrying out reactions for producing antibiotic pharmaceutical reagents, treating human blood for promoting desired chemical reactions such as decomposition of urea, hydrolyzing the disaccharide lactose to its constituent monosaccharides glucose and galactose (especially the lactose in milk and in cheese whey), isomerizing the aldose D-glucose to the sweeter ketose D-fructose, selectively deacylating acyl L-amino acid within a D-L mixture of amino acids, clotting milk for cheese production with the enzyme rennin, and many other useful and potentially useful purposes. A major advantage of using enzymes in such insoluble form bound to a solid supporting material is that the catalytically active enzyme may be physically retained in the reaction vessel and contacted there with a continuously flowing liquid process stream. Before it was possible to bond enzymes to such insoluble supports, the enzymes would remain in the liquid process stream or could be separated therefrom only with difficulty with the result that the enzyme could be reused only with difficulty or not at all. Now that the art exists for bonding enzymes to insoluble supports, it becomes possible to use them in much the same way as ordinary heterogeneous catalysts on inert, insoluble supporting carriers that are well known in the chemical process industry. Such use now permits the continuous, convenient reuse of the same insolubilized enzyme catalyst for contacting a continuously flowing liquid reaction process stream thereby catalyzing a desired chemical reaction within said stream but without the necessity of separating the enzyme from the reaction products or the possible disadvantage of losing said enzyme entirely and not being able to re-use it.

However, some major problems have been encountered in the practical application of such insolubilized enzymes. They have usually been bonded to natural and synthetic high polymers and then used in fixed bed reactors; in such systems disadvantageously high pressure drop and plugging have been encountered and this behavior can be attributed to the small particle size and to the deformable, gel-like properties of the polymeric supporting material. More recent attempts to circumvent these kinds of problems have involved using inorganic supporting materials such as apatite and glass. While the latter materials are less deformable than the organic polymeric supports, columns packed with these materials still are susceptible to plugging and cause high pressure drop when small particle sizes are used in fixed, packed beds. When the particles are made sufficiently large to avoid such adverse plugging and pressure-drop behavior, their very size causes large mass transfer resistances both within the liquid film surrounding the support particles and within the support particles themselves if they are porous. Such mass transfer resistance can prevent the reactants from reaching the immobilized enzyme as fast as they can react and thereby can result in inefficient utilization of the enzyme bound to the solid support. To minimize mass transfer resistances, both within the solid supporting particles themselves and in the liquid film surrounding them, the particles should be as small as possible. However, as has already been stated, fixed packed beds of small particles are markedly susceptible to plugging and cause disadvantageously high pressure drops. Stirred-tank, slurry reactors are also susceptible to plugging and have the added disadvantages of back mixing, mechanical complexity and high shear rates.

Until the present invention there has been no simple way of utilizing insolubilized enzymes bound to solid supporting materials in a process that simultaneously provides relative freedom from plugging and from high pressure drops, reasonably high liquid flow rates in approximate plug flow and excellent mass transfer rates from process stream to the solid supporting particles and within the particles themselves. The present invention employs an expanded or fluidized bed of insoluble support particles to which enzyme is bound but the present invention differs from prior art in that expanded of fluidized bed processing has never before been applied to enzyme catalyzed reactions, in that the insoluble, support particles must have certain type of properties for good fluidization behavior in a fast flowing liquid stream, and in that said good fluidization properties are achieved by constructing the insolubilized-enzyme, catalyst particles in new and different ways. It should be emphasized that the solid, immobilized-enzyme particles of the present invention may be porous or non porous. Often porous particles, or non porous particles surrounded by porous outer layers, will be chosen in order to provide more surface area within pores where enzyme can be bound.

SUMMARY OF THE INVENTION

It is an object of this invention to provide a means of carrying out enzyme-catalyzed reactions by a process which is not susceptible to plugging, which permits large flow rates of liquid reactant stream with low pressure drop and which employs enzymes bound to solid supporting material as carrier.

It is another object of this invention to provide a process with the above-described advantages and for the purpose stated above, that can also operate using small particles of supporting material to which enzyme catalyst is bound and which thereby provides high rates of mass transfer from the liquid stream to the enzyme catalyst particles and within these particles in the event they are porous.

It is a further object of this invention to provide such a process that also permits approximate plug flow with little backmixing of the liquid as if flows through the bed of enzymic catalyst particles.

Still another object of this invention is to provide insolubilized enzyme catalysts having properties of density and particle size suitable for conducting such processes as described above.

Yet another object of this invention is to provide methods of preparing insolubilized enzyme catalysts possessing such properties.

These and other objects have now herein been attained by a process in which the enzymes are insolubilized by binding them to the outer surface or non-porous, dense particles, or within the pores of dense porous particles, or to a thin layer (the layer may be porous or non-porous) or organic polymer or of glass on the outside surfaces of such particles, passing a steady stream of liquid reactant through a bed of such particles, the flow rate, viscosity and density of the liquid and the sizes and densities of the particles being of the values required to cause expansion or fluidization of the bed of particles and thereby providing the benefits of fluidized or expanded bed operation with a liquid stream flowing in approximate plug flow through the fluidized or expanded bed.

DEFINITIONS

Within this disclosure, the term expanded bed refers to a process wherein the particles of the bed are suspended and agitated by the liquid but do not mix or circulate within the bed to any appreciable extent, the term fluidized bed to a process wherein the suspended and agitated particles do circulate and mix within the bed, and the term suspended bed is generic to the terms fluidized bed and expanded bed and used to refer to either one or both of them. The term enzyme as used within this disclosure can refer to an enzyme, a coenzyme or an enzyme analogue which is a molecule synthesized to approximate the catalytically active structure of a natural enzyme and which has similar catalytic activity. The terms immobilized and insolubilized are used interchangeably throughout this disclosure to denote either chemical or physical binding of an enzyme to a carrier or entrapment of an enzyme within a carrier. The term solid particle within this disclosure is intended to refer to three-dimensional bodies comprising matter in substantially the solid state of aggregation, as contrasted to liquid or gaseous states of aggregation; such solid particles may be porous or non-porous and, if they are porous, such porosity may be uniform or nonuniform throughout the particle. The term theoretical density is meant to refer to the density of the material in the non porous form — that is, the density usually recorded in handbooks and reference books.

DESCRIPTION OF PREFERRED EMBODIMENTS

The embodiments discussed are presented herein for purposes of illustration only and are not intended to be limiting in any manner.

According to the present invention, one of the important properties of a useful insolubilized enzyme catalyst support or carrier is a density sufficiently large to permit the use of small particles and large liquid flow rates in expandedor fluidized-bed operation. Although insolubilized enzymes have been known or used for more than a decade, they have never before been employed in expanded or fluidized bed processes; one reason for this undoubtedly is the fact that in almost every instance the enzymes have been bound to materials of low density. The present invention calls for the use of particles of inert, high density materials such as non-corrodible metals or metal oxides as supporting material to which the enzyme or enzymes of choice are then bound.

The carrier or support for the enzymes as used in this invention can be particles of metallic nickel or nickel oxide sinter as supplied by the International Nickel Company, Inc. under the trade names Nickel Oxide Sinter 75 and Nickel Oxide Sinter 90. The density of this material is about 8 gm/cm$^3$ and an appropriate particle-size range is 10$\mu$m to 0.25 inch, for fluidization by water, although the preferred size range will depend on the density and viscosity of the fluidizing liquid. Enzymes may be bound to the nickel oxide material directly; metallic nickel particles can be partially oxidized in order to develop a coating of nickel oxide on their surface by exposing them to an air or oxygen atmosphere at high temperature. As reported by Weetall and coworkers [Biochim. Biophys Acta 206, pp 54–60 (1970)] an alkylaminosilane derivative of the oxide may then be prepared by refluxing the oxide coated support particles about 24 hours in a toluene solution containing about 10% $\gamma$-aminopropyltriethoxysilane. The particles are then washed in solvents such as toluene and acetone, dried under vacuum at 60° C, and then the alkylamino group on the particles is acylated by refluxing for about 24 hours in a chloroform solution containing 10% p-nitrobenzoyl chloride and 10% triethyl amine. After washing with chloroform and drying at 60° C under vacuum the aryl nitro group on the particles is reduced to an aryl amino group by refluxing for about one hour in an aqueous solution of 10% sodium dithionite. After washing with water and drying, the particles are then diazotized by reaction with an aqueous solution containing about 2.5% of sodium nitrite in 2N HCl under conditions of 0° C and gentle aspiration to remove evolved NO$_2$. This reaction is complete after about 20 minutes whereupon the particles are filtered and washed with cold aqueous sulfamic acid (about 1%) and then immediately contacted with an appropriate buffer solution of the enzyme of choice which is thereby coupled to the particle by a diazo type bond. This diazo type bond has been used successfully to insolubilize L-amino acid oxidase [Weetall and Baum, Biotech. & Bioeng. XII, pp. 399–407 (1970)], urease [Weetall and Hersh, Biochim. Biophys Acta 185, pp. 464–465 (1969)], alkaline phosphatase [Weetall, Nature 223, p. 959 (1969)], trypsin and papain [Weetall, Science 166, pp. 615–617 (1969)] and nicotinamide adenine dinucleotide (NAD) [Weibel, et al., Biochem and Biophys Res Comm 44, pp 347–352 (1971)]. In each of these cases the enzyme coupling reaction should be carried out under mild conditions: aqueous medium, low temperature and a pH near the neutral point. After coupling to the enzyme the particles are used in a liquid fluidized bed reactor.

Another type of chemical bond that can be used to couple an enzyme to a metal oxide is that formed between the enzyme and an isothiocyanate group attached to the solid. To do this the metal oxide is refluxed as described above with $\gamma$-aminopropyltrietroxysilane solution in toluene and the resulting alkylamine derivative is then refluxed overnight in a 10% solution of thiophosgene in chloroform, washed with chloroform, dried and immediately contacted with an appropriately buffered solution of the enzyme of interest. This type of chemical bonding has been used to immobilize trypsin, ficin, papain and glucose oxidase [Weetall, Biochem. Biophys.Acta 212, pp. 1–7 (1970)] and several other enzymes [Manecke, Biochem. Journal 107, pp. 2–3P, (1968)]. Various techniques for bonding a variety of enzymes to inorganic carriers using silane coupling agents have been disclosed and claimed in U.S. Pat. No. 3,519,538 to Messing et al.

It is evident that many other kinds of chemical bonds can be employed to attach enzymes to a dense, particulate carrier suitable for expanded-or fluidized-bed operation without departing from the substance of the present invention; the various types of chemical bond that have been successfully employed are part of the established art and are described in published literature [e.g. Kay, Process Biochemistry 3, 36 (1968) and Brown et al., Enzymologia 35, 215 (1968)]. It is also evident that it is possible to practice the present invention using various other types of dense particulate material to which the enzyme of choice is then bound. By proper selection of these materials it is possible to vary the density of the insolubilized enzyme catalyst particles over a wide range; for example it is possible to use glass (density 2.5 gm/cm$^3$), nickel (density 8.9 gm/cm$^3$), iron or preferably stainless steel (density about 8 gm/cm$^3$), silver (density 10.5 gm/cm$^3$), molybdenum (density 10.2 gm/cm$^3$), tantalum (density 16.6 gm/cm$^3$), gold or tungsten (density 19.3 gm/cm$^3$), rhodium (density 21.4 gm/cm$^3$), platinum (density 21.5 gm/cm$^3$) various alloys of these metals. The foregoing densities are theoretical densities which generally apply to the stated materials in the non-porous state; such densities are the values found in handbooks and other reference works. Various oxides, hydroxides, carbides, silicates and other insoluble chemical compounds of dense chemical elements may be used as such carriers. Clearly the metals, alloys or similar materials should also be chosen for inertness, resistance to the particular aqueous environment to be employed and for properties of non-interference with the particular enzyme and chemical reaction system to be employed. It is evident that a wide variety of materials can be used for these carrier particles.

When it is possible to form a tough, tenacious, insoluble and otherwise suitable oxide coating on metallic particles of the proper density, the enzyme of choice can be bound to the oxide by one of the techniques outlined above in which the oxide is silanized to produce alkylsilane groups on the surface as a first step. It is clear that it is also possible to use particles of the metal oxide itself as the carrier material using these procedures. Another possible approach, however, is to first coat the particles with a suitable polymer and then use one of the many known techniques for chemically bonding the enzyme of choice to the polymer. These techniques for bonding enzymes to polymers, which are part of the established art, have been discussed by Goldstein and Katchalski [Zeitschrift fur analytische Chemie 243, p. 375 (1968)] and Manecke [Proceedings of the Biochemical Society, page 2 P, (January 1968)] and they include the use of derivatives of polymers such as cellulose, polystyrene, copolymers of leucine and phenylalanine, copolymers of methacrylic acid, methylacryl-3-fluoroanilide and divinyl benzene, copolymers of methacrylic acid, fluorostyrene and divinyl benzene, polymers of m-isothiocyanatostyrene and vinylisothiocyanate and chemical bonds such as azide, diazo, isocyanato, isothiocyanato, carbodiimide and sulfonamide; enzymes that have been bound by these techniques include glucose oxidase, papain, ficin, trypsin, urease, diastase, invertase, chymotrypsin and alcohol dehydrogenase. An alternative but similar approach is to coat the dense carrier particles with glass by using the fine particles glazes and sealants supplied by Owens-Illinois and by Corning Glass and then to bond the enzyme of choice to this glass layer using one of the techniques described above for bonding enzymes to metallic oxides that begins by refluxing the glass-coated particles with a toluene solution of γ-aminopropyltriethoxysilane.

There are many procedures known in the art to coat dense particles (such as of a metal or a metallic oxide with layers of polymer or of glass. Almost any recognized film forming technique can be used for coating with a polymer. For example, the particles can be simply contacted with a solution of the polymer of choice, after which the particles are filtered and dried to remove the solvent and leave a layer of polymer on their surfaces. An alternative approach is to produce the polymer or copolymer by polymerization within a solution in which the particles of choice are suspended; as the polymer forms and grows in solution it will tend to deposit on the particles which can then be filtered and dried. In this latter technique it is possible to control the molecular weight and porosity of the polymer deposited on the particles by controlling temperature and concentrations of monomer, solvent and crosslinking agent present in the mixture. Adhesion between the dense particles and the polymer can often be improved by first coating with a bonding latex such as the Accobond resins supplied by the American Cyanamid Company, in accord with the manufacturer's instructions. To coat metallic particles with glass they can be contacted with a suspension of a glass frit such as the sealants mentioned above which have particles which pass a 325 mesh screen; then the metal particles coated with the glass particles are dried and baked in a furnace to bond the glass to the metal; it is possible to control the porosity and particle size of the resulting layer of glass on the metal by proper choice of glass frit size and baking temperature.

In addition to chemical attachment of enzymes to polymers, glass and solid oxides it is also possible to prepare waterinsoluble derivatives of enzymes by physical adsorption onto colloidal particles, by entrapment of enzymes within insoluble matrices of cross-linked polymers and by chemical crosslinking of an enzyme by a bifunctional reagent. All of these techniques for preparing water-insoluble derivatives of enzymes are known in the art and have been described in the published chemical literature. It will be obvious to one possessing ordinary skill in the art how to adapt these various techniques for enzyme insolubilization to forming thin films of enzyme or enzyme-bearing material on the surfaces of small, dense particles suitable for use in the present invention. For example, colloidal particles may first be bonded to the surface of the dense particles suitable for fluidization in the present invention followed by adsorption of enzyme within the porous layer of colloidal particles thus formed. Alternatively, cross-linked polymers containing entrapped enzymes may be bonded to the dense, small particles specified in the present invention or these particles may be coated with an insoluble layer of cross-linked enzymes. With reference to the discussion above, when the carrier particles comprise dense cores surrounded by layers of less dense material to which the enzyme is attached, it is usually preferable that the outer shell be relatively porous and the inner core non-porous. For example, if glass is to be used as the core it will usually be better to use a non-porous glass for the core in order to impart greater density to the core as well as because non-porous glass is frequently stronger and cheaper than porous glass.

Preparation of enzyme catalysts immobilized by bonding to dense particles as described herein permits their use in expanded-bed or fluidized-bed reactors in which the particles are maintained in fluidized suspension by the flow of a stream of liquid (which contains the substrate or reactant) through the bed. Such liquid fluidization provides the advantages of approximate plug flow of the liquid through the bed in contrast to a stirred, slurry-type reactor and also relative freedom from plugging and from high pressure drop in contrast to fixed-bed operation. In the usual type of fluidized operation the fluidized particles will be well mixed within the bed but it is possible to avoid the mixing of the particles from one part of the bed to another by packing the bed with larger particles which do not move or mix themselves and thereby prevent the small enzyme-bearing particles from mixing within the bed, but at the same time permit the fluidization of the small particles within the interstices of the packed large particles. Such packed, fluidized beds as described by Gabor [Chem.Eng.Progr.Symp. Series. No. 62, 62, 302 (1966)] and Gabor et al. [Chem.Eng. Progr.Symp. Series No. 42, 60, 96 (1964)] also fall within the purview of the present invention.

The use of dense materials for the particles which carry the enzyme permits good fluidization while using particles of small size; using such small particles increases mass-transfer rates of reactants to the particles and therefore also increases the rate of chemical reaction. Furthermore, the use of dense, enzyme-carrier particles has the added advantage of permitting high liquid flow rates through the expanded- or fluidized-bed without entrainment and loss of the particles from the bed. The higher liquid flow rates and higher rates of reaction that can be realized in this kind of system using small, dense particles as catalyst carrier provides still another important advantage of high production rate of reaction product from this type of reactor. These and other advantages will be more apparent from the examples which follow.

Having generally described the invention, a further understanding can be obtained by reference to certain specific examples which are presented herein for purposes of illustration only and are not to be limiting in any manner.

EXAMPLES

The superiority of suspended or fluidized-bed operation of liquid plug-flow reactors using as catalysts enzymes bound to small, dense particles is demonstrated herein by design calculations for a reaction, the global or net rate of which is about equal to the rate of mass transfer of the reactant from the bulk solution to the surface of the solid, enzyme-bearing particles; i.e. for a situation in which the rate of chemical reaction is controlled by mass transfer to the catalytic particle. These computations have been carried out for reaction of a dilute aqueous solution of ethanol containing excess NAD using the Ergun Equation for pressure drop in flow through beds of solid particles [see *Principles of Unit Operations* by Foust et al., p. 475, equation 22.86, John Wiley & Sons, Inc. (1960) or *Unit Operations of Chemical Engineering* by McCabe and Smith (2nd. ed.) p. 161, equation 7-26, McGraw-Hill Book Company (1971)], correlations for mass transfer coefficients in fixed and in packed beds of particles [see *Chemical Engineering Kinetics* by J. M. Smith, pp. 380–383, equations 10-36 through 10-39 and Figure 10-2 on p. 364, McGraw-Hill Book Company (1970)], a smoothed correlation of particulate fluidization [see *Fluidization and Fluid-Particle Systems* by Zenz and Othmer, p. 236, Figure 7.7, Reihold Publishing Co. (1960)], and the common, well known design equation for plug-flow reactors. Assuming that the reactant is ethanol in aqueous solution in which the diffusivity of ethanol is about $10^{-5}$ cm$^2$/sec [i.e. a dimensionless Schmidt Number equal to 1000 as would be the case for a dilute aqueous solution of ethanol reactant], that the reactor effects a conversion of said ethanol reactant equal to 99.9 percent, that the liquid reactant solution is passed in plug flow through beds of approximately spherical particles of approximately uniform diameter in each type of reactor, and assuming further that the flow rate of said liquid reactant solution is 70,000 lb/hr, ft$^2$ of reactor cross section and that the said liquid reactant solution has viscosity equal to 1 centipoise and density equal to 1 gm/cm$^3$, the following results are computed for different particle sizes, different particle densities, and two different types of reactor:

1. a fixed-bed reactor in which the particles of enzymic catalyst remain packed in an immobile bed, and
2. fluidized-bed reactors in which the particles of enzymic catalysts are suspended and agitated by the motion of the liquid through the reactor.

EXAMPLE I

Conversion of ethanol by reactor = 99.9%, Schmidt Number = 1000, Viscosity of reactant feed = 1 centipoise, Density of reactant feed = 1 gm/cm$^3$, Mass flow rate of reactant feed = 70,000 lb/hr, ft$^2$ of reactor cross section.

| Reactor Type | Particle Diameter | Particle Density | Bed Porosity | Reactor Pressure Drop | Reactor Length |
|---|---|---|---|---|---|
| fixed bed | 5325 μm | imma-terial | ~0.36 | 95 psia | 49.5 ft |
| fluid bed | 500μm | 8.6 gm/cm$^3$ | ~0.8 | 7.9 | 4.8 |
| " | " | 16.6 | ~0.7 | 12.8 | 2.8 |
| " | " | 19.3 | ~0.65 | 14.8 | 2.6 |
| " | 300 μm | 16.6 | ~0.8 | 7.7 | 2.9 |
| " | " | 19.3 | ~0.75 | 8.7 | 2.4 |

It is to be noted for the results of Example I that the reactor length necessary to carry out the specified reaction is an order of magnitude larger when a fixed bed reactor packed with catalyst particles of about 5300μm or 0.53 cm diameter is employed in contrast to the reactor lengths required for fluidized-bed reactors containing catalyst particles of about 500μm or 300μm diameter. With regard to these same results it is also noteworthy that the pressure drop required for the fluidized-bed reactor for this reaction is between 6- and 12-times lower than for the fixed-bed reactor.

It has been demonstrated, therefore, that, compared to a fixed bed reactor carrying out the identical reaction, the fluidized bed reactors possess the dual advantages of much lower pressure drop and much smaller size. The required length and pressure drop of the fixed-bed reactor could be lowered somewhat by packing it with smaller particles of enzymic catalyst but this would make the reactor far more susceptible to plugging which would eventually lead to still larger pressure drop across this reactor. Likewise, the pressure drop across the fixed bed reactor could be diminished somewhat by packing it with larger catalytic particles but this would increase still further the length of the reactor required for the stated conversion of reactant. With regard to particle size and density, for the feed flow rate, density and viscosity of the present example, it would be impossible to use 500$\mu$m diameter particles of density 2.5 gm/cm$^3$ or lower, or even 300$\mu$m diameter particles of density 8.6 gm/cm$^3$ or lower in fluidized-bed operation; if this were attempted the catalyst particles would be swept from the reactor; however, denser particles can be kept in the reactors under these conditions. This clearly demonstrates the advantages of using catalysts comprising enzymes attached to very dense particles to permit the use of small particles in these kinds of fluidized reactors. The advantages of the fluidized-bed reactors would be amplified still further if the reactant feed solution were moe viscous, for example a glucose solution that might have a viscosity of 100 centipoises or more. A more viscous reactant solution would also further amplify the advantages of high density for the immobilized enzyme catalyst particles.

In the next example the same reaction is considered except that the length of the reactor is fixed and the percentage conversion of the reactant is computed:

EXAMPLE II

Reactor length = 1 foot, Schmidt Number = 1000, Viscosity of reactant feed = 1 centipoise, Density of reactant feed = 1 gm/cm$^3$, Mass flow rate of reactant feed = 70,000 lb/hr, ft$^2$ of reactor cross section.

| Reactor Type | Particle Diameter | Particle Density | Bed Porosity | Reactor Pressure Drop | Conversion of Reactant |
|---|---|---|---|---|---|
| fixed bed | 5325 $\mu$m | immaterial | 0.36 | 1.92 psia | 13.8% |
| fluid bed | 500 | 8.6 gm/cm$^3$ | ~0.8 | 1.64 | 76.2 |
| " | 500 | 16.6 | ~0.7 | 4.57 | 91.6 |
| " | 500 | 19.3 | ~0.65 | 5.70 | 93.0 |
| " | 300 | 16.6 | ~0.8 | 2.65 | 90.7 |
| " | 300 | 19.3 | ~0.75 | 3.63 | 94.4 |

Example II demonstrates that much larger conversion of reactant can be accomplished by fluidized-bed reactors using enzymic catalysts bound to dense particles of diameters 300$\mu$m and 500$\mu$m, in contrast to a fixed-bed reactor packed with catalytic particles of about 5300$\mu$m diameter. If particle size were lowered or length increased for the fixed-bed reactor of Example II in order to improve the conversion, the pressure drop would quickly become disadvantageously large. Example II further demonstrates the increases in conversion that can be obtained in a fluidized reactor by decreasing the size and increasing the density of the particles to which the enzymic catalyst is bound. As in the case of Example I, the advantages of fluidized-bed operation and of dense particles of insolubilized enzymic catalyst would be further amplified for Example II also if more viscous reactant feed were employed.

In the examples described herein the reactant or substrate has been specified as ethanol and the computed results have been based on a rate of chemical reaction assumed equal to the rate at which ethanol is transported from the bulk solution to the surfaces of the enzyme-bearing particles where chemical reaction takes place. A suitable reaction would be the dehydrogenation of ethanol for which an alcohol dehydrogenase enzyme could be bound to the particles. As mentioned elsewhere in this specification alcohol dehydrogenase has been successfully bound to various polymeric carrier materials so a suitable enzyme carrier could be formed by a metal particle coated with an appropriate polymer. Clearly, if another reactant must react with the substrate (e.g. NAD with ethanol in the instant Examples) it, too, must be present in sufficient concentration in the solution. Other substrates and reactions can be substituted for the alcohol dehydrogenation of the instant Examples, provided the appropriate enzymes are also substituted as the catalysts and the necessary reactants or coenzymes are also present in the feed solution in sufficient concentration. To compute the results for another such reaction system it is necessary to modify the diffusivity or Schmidt Number to make it conform with that reactant which limits the rate of reaction by its rate of transport from the bulk solution to the surface of the solid.

In practice a suitable representative configuration for the fluidized-bed reactor in the instant Examples is a glass or metal tube in a vertical position with a screen or support grid spanning the lumen of the tube near the bottom. The openings of the supporting screen or grid should be sufficiently small to prevent passage of the particles of the bed but not so small as to cause unnecessarily large pressure drops. Appropriate sizes for the instant Examples are holes of about 250$\mu$m in the support grid and a reactor-tube diameter of about 4 inches. The particles of enzyme catalyst are placed in the tube and are supported by the grid when the reactor is not in operation. Reactions are carried out under fluidization conditions by passing the feed solution upwards through the reactor at the appropriate flow rate.

One of the major advantages of fluidized-bed reactors for enzymic processing is a lessened tendency toward plugging or stoppage, even under conditions when a fixed-bed reactor would rapidly plug (e.g. due to growth of microorganisms within the bed); for this reason it may not always be prudent to use a screen or support grid which would also tend to plug. It has been found that such a screen or support grid is not necessary if the entrance to the bottom of the fluidized reactor is gently tapered in the shape of a cone from the small diameter of the inlet feed pipe to the larger reactor diameter. A valve in the feed pipe can be closed to prevent loss of particles by settling through the feed pipe at the bottom of the inlet cone; this valve would be opened only after activation of pumping means to cause the liquid to flow through the reactor.

In the foregoing examples computations have been carried out on the basis of spherical particles. In practice the particles will frequently be somewhat irregular and uneven due to the fact that readily available particulate supports will often be manufactured by a grinding, pelleting, prilling or spray-drying step before attaching enzyme thereto. In any event such particles will ordinarily fall within a size range (based on the largest overall particle dimension) of from about 7 to 70,000 micrometers and their densities will usually fall within the range of about 1 to 25 grams/cubic centimeter. In general the choice of particle size and particle density will depend on the density, viscosity and flow rate of the fluid reactant stream. The use of denser particles will permit the use of smaller particle sizes under a given set of conditions of fluid density, viscosity and flow rate whereas the use of larger-size particles will permit their density to be lower. On the other hand, for increased density and/or viscosity of the fluid reactant stream it will generally be desirable to choose larger and/or denser particles. In general, a denser and/or more viscous fluid medium will occasion the use of denser particles if it is desired to keep particle size small or, of it is desired to keep the particle density low, then larger particles might be employed to compensate for the increased density and/or viscosity of the fluid. For a given set of fluid conditions it will often be desired to use denser particles in order that their sizes may be chosen small; on the other hand if larger particle sizes are desired then it will often be prudent to use lower particle densities.

The fluidized- or expanded-bed reactors in which enzyme-bearing catalytic particles are maintained in a state of agitation and suspension, and in many cases caused to mix or circulate within the reaction zone, by the flow of liquid, as set forth in the present invention, can be used for a variety of chemical processing applications. For example, the reactor systems of the present invention can be used for converting starch to glucose, for inverting sugars, for oxidizing glucose, for decomposing urea or hydrogen peroxide, for lysing lipids, proteins, peptides and other molecules, for dehydrogenating alcohol, for oxidizing lipids, and for many other uses. They should find application for carrying out any enzyme-catalyzed reaction for which the enzyme can be immobilized on a solid, particulate carrier material.

Fluidized-bed reactors should be especially well suited for the coagulation or clotting of milk as a preliminary step in the production of cheese using the enzyme rennin or rennet immobilized on particles in a fluidized bed through which the milk is passed. The traditional source of rennet has been from calf stomachs but in recent years there has been a tendency to use a microbial rennet enzyme derived from the fungi *Mucor miehei* and *Mucor pusillus;* in the present invention enzyme from either source would be used in a fluidized bed in immobilized form.

Enzymatic processing in fluidized beds is also very advantageous for the conversion of starch to dextrins, to glucose and to high-fructose syrup. The enzyme α-amylase can be attached to the solid supports described herein and used in fluidized beds for catalyzing the liquefaction of starch, thereby hydrolyzing starch molecules to dextrins; the enzyme glucoamylase can be used similarly in fluidized beds to catalyze the hydrolysis of dextrins and starch to glucose; the enzyme glucose isomerase can also be used in fluidized beds to isomerize D-glucose to the sweeter ketosugar D-fructose or levulose. Various aspects of these enzymatic processes are disclosed in U.S. Pat. Nos. 3,910,821 to Cory; 3,616,221 to Takasaki et al.; 3,694,312 to Loyd et al.; 2,950,228 to Marshall; 3,783,101 to Tomb et al.; 3,868,304 to Messing and 3,705,084 to Reynolds.

Other important applications of fluidized beds of immobilized enzymes are: the use of immobilized α-galactosidase or melibiase (which can be obtained from the fungus *Mortierella vinaceae*) for hydrolyzing sugar raffinose in beet sugar molasses (this raffinose forms in beets during cold weather and retards the rate of sucrose precipitation from the beet sugar molasses); the use of the immobilized enzyme aminoacylase to selectively hydrolyze acryl-L-amino acid within a mixture of acyl-DL-amino acid thereby facilitating the downstream separation of the L-amino acid from the mixture according to the process disclosed by Chibata et al. in U.S. Pat. No. 3,386,888; the use of immobilized aspartase to catalyze the addition of ammonia to fumaric acid thereby producing L-aspartic acid; the use of immobilized penicillin amidase to hydrolyze penicillin to 6-aminopenicillanic acid, a precursor of various important penicillin derivatives; the use of immobilized glucose oxidase and catalase (preferably within the same reactor or even immobilized together on the same fluidizable particles) to produce gluconic acid by the oxidation of glucose using oxygen; the use of immobilized sulfhydryl oxidase to catalyze the oxidation of sulfhydryl groups in milk by oxygen thereby improving the temperature stability of the milk; the use of immobilized pectinases for clarifying fruit juices and alcoholic beverages; the use of immobilized invertase to hydrolyze sucrose to invert sugar; the use of immobilized isoamylase and α-amylase to hydrolyze starch and starch dextrins to maltose; the use of immobilized galactose oxidase to oxidize galactose to galactonic acid; the use of immobilized galactose oxidase and lactase (preferably within the same reactor or even immobilized on the same fluidizable particle) to convert lactose in milk, milk products, and cheese whey to a mixture of glucose and galactonic acid; the use of immobilized βglucanases to reduce beer viscosity; the use of immobilized polyphenol oxidase to oxidize polyphenols in beer wort; the use of immobilized papain in the chill-proofing of beer.

Having fully described the invention, it will be apparent to one having ordinary skill in the art that many modifications and changes can be made without departing from the spirit or scope thereof. For example it is possible to carry out the present invention for many different types of enzyme-catalyzed reactions, using reactors of many different types of construction and mechanical design and by preparing many different kinds of enzyme-bearing particles of appropriate small particle size and high density suitable for use in such reactors. It is also possible to carry out the present invention while simultaneously removing particles of insolubilized-enzyme catalyst from the reactor, regenerating said catalyst particles in a separate vessel and returning said regenerated catalyst particles to the reactor.

What is claimed is:

1. An improved method of effecting enzymatic reactions in a reactant material which is contained in a carrier fluid by passing the carrier fluid past enzyme material attached to a supporting material comprising:
   a. passing the carrier fluid generally upwardly through a reaction zone containing finely divided particles having a size range of 0.01 millimeters to 5 millimeters to which the enzyme material is attached, said particles composed essentially of material having a theoretical density of from about 2.4 grams/cm$^3$ to 25 grams/cm$^3$, the volume of the reaction zone being sufficient to contain all of the particulate supporting material in at least an expanded condition wherein the various particles are substantially not supported upon each other,
   b. maintaining an upward velocity of carrier fluid through said reaction zone sufficient to suspend and agitate the said particulate supporting material, but insufficient to carry said particulate supporting material from reaction zone.

2. The improved method of claim 1 wherein said particles are composed essentially of material having a theoretical density not less than about 3 grams/cm$^3$.

3. The improved method of claim 2 wherein the particulate supporting material is selected from the groups consisting of metals and metal oxides.

4. The method according to claim 1 wherein said supporting particles comprise dense cores surrounded by less dense material to which said enzyme is attached.

5. The method of claim 4 wherein said dense cores are of material selected from the groups consisting of metals and metal oxides.

6. The method of claim 1 wherein the said supporting particles employed are of smaller size when their density is large and of larger size when their density is small and the said reactant-containing fluid is essentially equivalent to water in density and viscosity.

7. The method of claim 1 wherein said supporting particles are of larger sizes and larger densities when the viscosity or the density of the said fluid is substantially larger than that of water.

8. The method of claim 1 wherein the enzyme material is selected from the group consisting of glucose isomerase, aminoacylase, aspartase, penicillin amidase, lactase and glucoamylase.

9. The method of claim 1 wherein the enzyme material is selected from the group consisting of rennin, alphaamylase, isoamylase, alpha galactosidase, catalase, sulfhydryl oxidase, pectinase, invertase, galactose oxidase, beta gluconase, polyphenol oxidase and papain.

10. Apparatus for conducting enzymic reactions wherein enzymes are immobilized on particles that are fluidized by the upward flow of carrier fluid containing a reactant material, comprising tube means forming a reaction vessel, enzyme material immobilized on insoluble supporting particles within said reaction vessel, said particles having sizes ranging from about 0.01 millimeter to 5 millimeters and composed essentially of material having a theoretical density ranging from about 2.4 grams/cm$^3$ to about 25 grams/cm$^3$, pumping means for causing flow of carrier fluid upwards through said enzyme-bearing particles, with the restriction that the dimensions of said reaction vessel, the sizes and densities of said particles, and the characteristics of said pumping means are such as to result in fluidization of said particles while permitting said particles to remain within said vessel, when said carrier fluid is caused to flow through the said vessel.

11. Apparatus according to claim 10 wherein said supporting particles are of materials selected from the groups consisting of metals and metal oxides.

12. Apparatus according to claim 10 wherein said supporting particles comprise dense cores surrounding by layers of less dense material to which said enzyme is attached.

13. Apparatus according to claim 12 wherein said dense cores are of material selected from the groups consisting of metals and metal oxides.

* * * * *